(12) United States Patent
Bavykin

(10) Patent No.: US 7,871,764 B1
(45) Date of Patent: Jan. 18, 2011

(54) UNIVERSAL NUCLEIC ACIDS SAMPLE PREPARATION METHOD FOR CELLS, SPORES AND THEIR MIXTURE

(75) Inventor: Sergei Bavykin, Darien, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 326 days.

(21) Appl. No.: 12/050,508

(22) Filed: Mar. 18, 2008

(51) Int. Cl.
*C12Q 1/00* (2006.01)
*C12Q 1/68* (2006.01)
*C07H 21/00* (2006.01)
*C07H 21/02* (2006.01)

(52) U.S. Cl. ............... 435/4; 435/6; 536/22.1; 536/25.4; 536/25.41

(58) Field of Classification Search ............ 435/6, 435/4; 536/25.4, 25.41, 22.1
See application file for complete search history.

(56) References Cited

U.S. PATENT DOCUMENTS

| | | | | | |
|---|---|---|---|---|---|
| 4,900,677 | A | * | 2/1990 | Hewitt | 435/259 |
| 4,935,342 | A | * | 6/1990 | Seligson et al. | 435/6 |
| 5,075,430 | A | * | 12/1991 | Little | 536/25.41 |
| 5,155,018 | A | * | 10/1992 | Gillespie et al. | 536/23.1 |
| 5,234,809 | A | * | 8/1993 | Boom et al. | 435/91.2 |
| 5,606,046 | A | * | 2/1997 | Woodard et al. | 536/25.4 |
| 6,180,778 | B1 | * | 1/2001 | Bastian et al. | 536/25.4 |
| 6,218,531 | B1 | * | 4/2001 | Ekenberg | 536/25.41 |
| 6,548,253 | B1 | * | 4/2003 | Holschuh et al. | 435/6 |
| 6,818,398 | B2 | * | 11/2004 | Bavykin et al. | 435/6 |
| 7,208,269 | B2 | * | 4/2007 | Bavykin et al. | 435/6 |
| 7,208,271 | B2 | * | 4/2007 | Bost et al. | 435/6 |
| 7,537,898 | B2 | * | 5/2009 | Bost et al. | 435/6 |
| 7,572,578 | B2 | * | 8/2009 | Mori et al. | 435/6 |
| 2002/0156037 | A1 | * | 10/2002 | Volkin et al. | 514/44 |
| 2003/0170664 | A1 | * | 9/2003 | Mori et al. | 435/6 |
| 2004/0019196 | A1 | * | 1/2004 | Bair et al. | 536/25.4 |
| 2009/0047724 | A1 | * | 2/2009 | Hillebrand | 435/219 |

OTHER PUBLICATIONS

Bavykin et al., Portable system for microbial sample preparation and oligonucleotide microarray analysis. Applied and Environmental Microbiology 67 (2): 922-928 (2001).*
Bavykin et al., Use of 16S rRNA, 23S rRNA, and gyrB Gene Sequence Analysis To Determine Phylogenetic Relationships of *Bacillus cereus* Group Microorganisms . J. of Clinical Microbiology 42(8): 3711-3730 (2004).*
Bavykin et al., Erratum. Use of 16S rRNA, 23S rRNA, and gyrB Gene Sequence Analysis To Determine Phylogenetic Relationships of *Bacillus cereus* Group Microorganisms . J. of Clinical Microbiology 44(7): 2676 (2006).*
Belgrader et al., "A Minisonicator to Rapidly Disrupt Bacterial Spores for DNA analysis," Analytical Chemistry 71:4232-4236 (1999).*
Chandler et al., "Continuous Spore Disruption Using Rapidly Focused, High-Frequency Ultrasound," Analytical Chemistry 73: 3784-3789 (2001).*
Dose et al., DNA Stability and survival of *Bacillus subtilis* spores in extreme dryness. Published in Origins of Life and Evolution of the Biosphere 25:277-293(1995).*
Kelly et al.. Radical generating coordination complexes as tools for rapid and effective fragmentation and fluorescent labeling of nucleic acids for microchip hybridization. Analytical Biochemistry 311: 103-118 (2002).*
Kuske et al., "Small Scale DNA Sample Preparation Method for Field PCR Detection of Microbial Cells and Spores in Soil," Applied and Environmental Microbiology 64(7): 2463-2472 (1998).*
Luna et al., Novel Sample Preparation Method for Safe and Rapid Detection of *Bacillus antrhacis* Spores in Environmental Powders and Nasal Swabs. Journal of Clinical Microbiology 41(3):1252-1255 (2003).*
McCormick, RM., A Solid-Phase Extraction porocedure for DNA purification. Analytical Biochemistry 181: 66-74 (1989).*
Moeller et al., "A Method for Extracting RNA from Dormant and Germinating *Bacillus subtilis* Strain 168 Endospores," Current Microbiology . 53: 227-231 (2006).*
Sakakibara et al., "Defined conditions for DNA Extraction from *Bacillus subtilis* Spores," Biochim Biohpys. Acta, 199: 548-550 (1970).*
Sargent et al., A Procedure for Isolating High Quality DNA from Spores of *Bacillus subtilis* 168 Journal of General Microbiology 116: 511-514 (1980).*
Vogelstein et al., Preparative and analytical purification of DNA from agarose. PNAS 76(2): 615-619 (1979).*

* cited by examiner

*Primary Examiner*—Ethan Whisenant
(74) *Attorney, Agent, or Firm*—Brian J. Lally; Mark P. Dvorscak; John T. Lucas

(57) ABSTRACT

The present invention relates to a method for extracting nucleic acids from biological samples. More specifically the invention relates to a universal method for extracting nucleic acids from unidentified biological samples. An advantage of the presently invented method is its ability to effectively and efficiently extract nucleic acids from a variety of different cell types including but not limited to prokaryotic or eukaryotic cells and/or recalcitrant organisms (i.e. spores). Unlike prior art methods which are focused on extracting nucleic acids from vegetative cell or spores, the present invention effectively extracts nucleic acids from spores, multiple cell types or mixtures thereof using a single method. Important that the invented method has demonstrated an ability to extract nucleic acids from spores and vegetative bacterial cells with similar levels effectiveness. The invented method employs a multi-step protocol which erodes the cell structure of the biological sample, isolates, labels, fragments nucleic acids and purifies labeled samples from the excess of dye.

18 Claims, 9 Drawing Sheets

Normalized Average Absolute Signal Per Probe
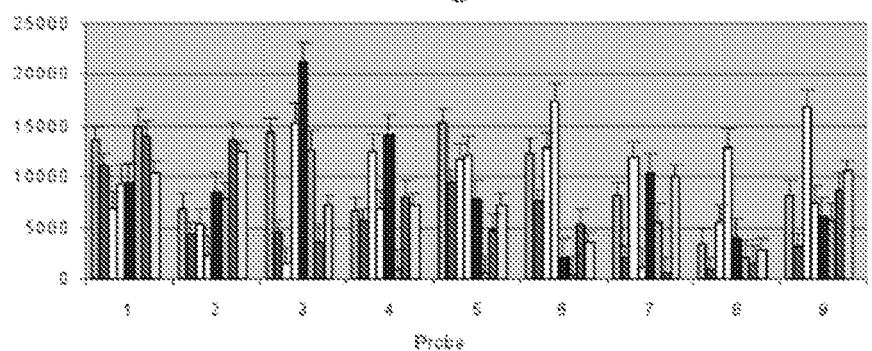
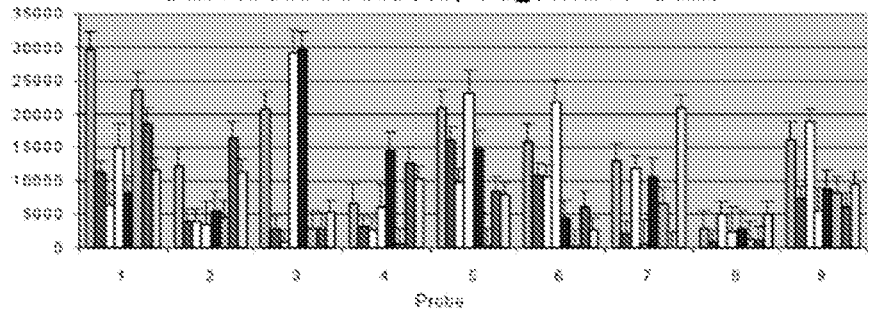
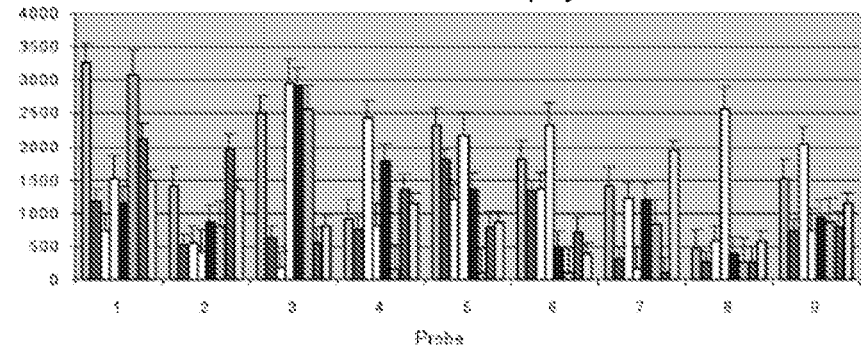
FIG. 1

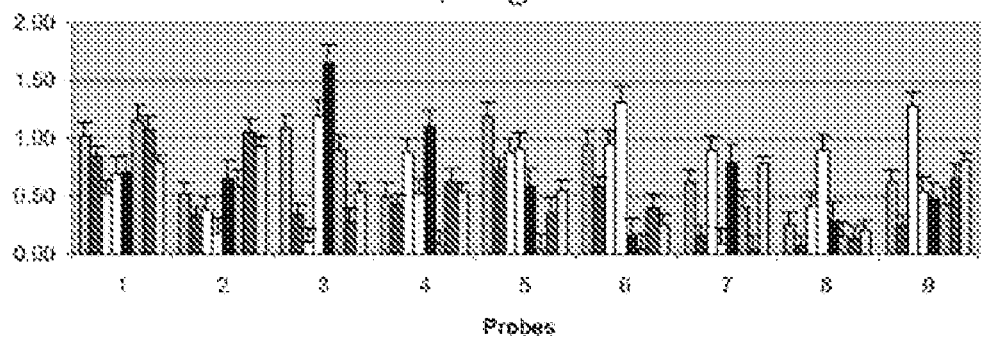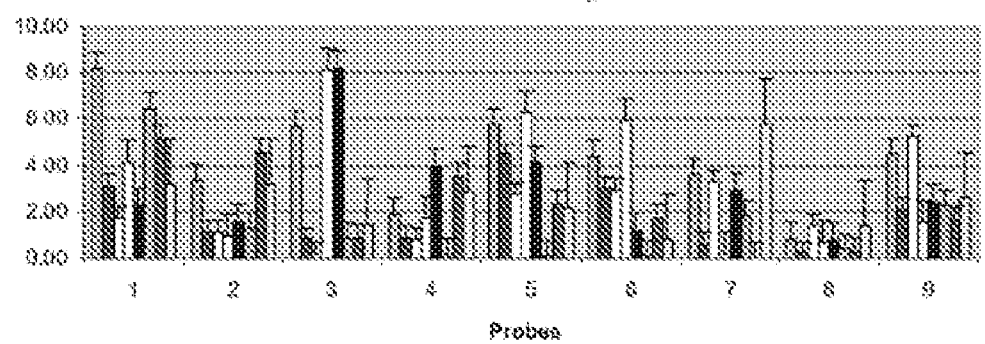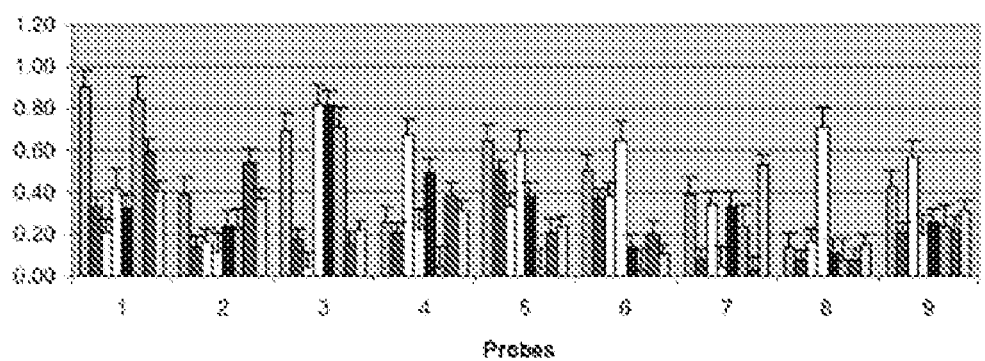
FIG. 3

Nucleic acid yield and summary statistics for S-Protocol versus U-Protocol

| | S-Protocol | | | | | | U-Protocol | | | | | | |
|---|---|---|---|---|---|---|---|---|---|---|---|---|---|
| | Vegetative cells | | | | | | Vegetative cells | | | Spores | | | |
| | VC-1 | VC-2 | VC-3 | VC-4 | VC-5 | | VC-1 | VC-2 | VC-3 | SP-1 | SP-2 | SP-3 | SP-4 |
| Yield (microgram) | 18.8 | 18.2* | 7.9 | 5.9 | 15.0 | | 38.5 | 39.2 | 32.8 | 43.7 | 43.5 | 53.0 | 48.6 |
| Av.Yield(microgram) | | 11.9 | | | | | | 36.9 | | | 47.2 | | |
| Stand.Dev. | | 6.0 | | | | | | 3.5 | | | 4.5 | | |
| Confidence, alpha=0.01 | | 7.8 | | | | | | 5.2 | | | 5.8 | | |
| Free dye | high | very high | high | high | high | | low | low | low | low | low | low | low |

*This value was discarded for summary statistics because the level of free dye made it difficult to accurately quantify nucleic acid yield

FIG. 7

Statistical Treatment of Hybridization Signals and Backgrounds to Estimate Method Sensitivity

| | S-Protocol | | | | | U-Protocol | | | | | | |
|---|---|---|---|---|---|---|---|---|---|---|---|---|
| | Vegetative cells | | | | | Vegetative cells | | | Spores | | | |
| | 1h, 20 ul (1.3 - 3.13 ug labeled nucleic acids, Av.=2.5 ug); Exp. 10 sec. | | | | | 1h, 20 ul (7.3 - 8.6 ug labeled nucleic acids, Av.=8.2 ug); Exp. 10 sec. | | | 1h, 20 ul (10.9-13.2 ug labeled nucleic acids, Av.=11.8ug); Exp 10 sec | | | |
| | VC-1 | VC-2 | VC-3 | VC-5 | | VC-1 | VC-2 | VC-3 | SP-1 | SP-2 | SP-3 | SP-4 |
| Average Total Signal | 55047 | 53403 | 63553 | 52960 | | 114025 | 97142 | 110509 | 41904 | 44590 | 65413 | 63034 |
| Average Sample Background | 26505 | 43863 | 42153 | 33237 | | 35518 | 24713 | 30515 | 31575 | 33213 | 50011 | 46984 |
| Av.Av. Sample Bckgr. | 36440 | For all replicate extracts | | | | 30249 | | | 40446 | | | |
| Standard Deviation | 8097 | | | | | 5408 | | | 9403 | | | |
| Confidence., alpha=0.01 | 10429 | | | | | 8042 | | | 12110 | | | |
| Average Absolute Sample Signal | 28542 | 9540 | 21400 | 19724 | | 78507 | 72430 | 79994 | 10329 | 11377 | 15402 | 16049 |
| Av.Av.Abs.Sample Signal | 19801 | For all replicate extracts | | | | 76977 | | | 13289 | | | |
| Standard Deviation | 7837 | | | | | 4008 | | | 2858 | | | |
| Confidence., alpha=0.01 | 10093 | | | | | 5960 | | | 3681 | | | |
| Average Absolute Signal/Average Background AvAvAbsSmpSign/AvAvSmpBckgr | 1.09 | 0.22 | 0.52 | 0.60 | | 2.23 | 2.97 | 2.64 | 0.33 | 0.34 | 0.31 | 0.35 |
| | 0.60 | For all replicate extracts | | | | 2.61 | | | 0.33 | | | |
| Standard Deviation | 0.36 | | | | | 0.37 | | | 0.01 | | | |
| Confidence., alpha=0.01 | 0.46 | | | | | 0.55 | | | 0.02 | | | |

Av. Total Signal was calculated as the average signal intensity for all 72 probes on each of the 6 replicate arrays.

FIG. 8

Recognition values for each sample extract and biochip.

| | S-Protocol | | | | | | | U-Protocol | | | | | | | | |
|---|---|---|---|---|---|---|---|---|---|---|---|---|---|---|---|---|
| | Vegetative Cells | | | | | | | Vegetative cells | | | | | Spores | | | |
| | VC-1 | VC-2 | VC-3 | VC-5 | | | | VC-1 | VC-2 | VC-3 | | | SP-1 | SP-2 | SP-3 | SP-4 |
| Array replicate → | 0.818 | 0.818 | 0.727 | 0.727 | 0.724 | Average | | 0.909 | 0.909 | 0.818 | 0.848 | Average | 0.727 | 0.727 | 0.909 | 0.727 |
| | 0.727 | 0.727 | 0.636 | 0.727 | 0.075 | SD | | 0.909 | 0.818 | 0.818 | 0.054 | SD | 0.909 | 0.818 | 0.727 | 0.818 |
| | 0.818 | 0.818 | 0.727 | 0.727 | 0.034 | Confidence | | 0.818 | 0.818 | 0.727 | 0.033 | Confidence | 0.909 | 0.818 | 0.727 | 0.727 |
| | 0.818 | 0.727 | 0.818 | 0.727 | | | Array replicate → | 0.818 | 0.909 | 0.818 | | | 0.727 | 0.727 | 0.909 | 0.818 |
| | 0.727 | 0.545 | 0.727 | 0.636 | | | | 0.909 | 0.818 | 0.909 | | | 0.818 | 0.727 | 0.818 | 0.818 |
| | 0.727 | 0.636 | 0.545 | 0.636 | | | | 0.818 | 0.909 | 0.818 | | | 0.909 | 0.909 | 0.727 | 0.727 |
| | 0.727 | 0.727 | 0.727 | 0.636 | | | | | | | | | | | | |
| | 0.818 | 0.727 | 0.818 | 0.727 | | | | | | | | | | | | |
| | 0.727 | 0.636 | | | | | | | | | | | | | | |

| | |
|---|---|
| | 0.803 Average |
| | 0.074 SD |
| | 0.039 Confidence |

Confidence values were calculated at alpha = 0.01.

FIG. 9

UNIVERSAL NUCLEIC ACIDS SAMPLE PREPARATION METHOD FOR CELLS, SPORES AND THEIR MIXTURE

STATEMENT OF GOVERNMENTAL SUPPORT

This invention was made during work supported by the U.S. Department of Energy under Contract No. W-31-109-ENG-38. Therefore, the United States Government has certain rights in this invention.

FIELD OF INVENTION

The present invention relates a unique method for extracting nucleic acids samples. More specifically one preferred embodiment of the invention relates to a method for effectively extracting nucleic acids from prokaryotic or eukaryotic cells, spores, or their mixtures in biological samples and further purification, labeling and fragmentation of the extracted nucleic acids.

BACKGROUND OF INVENTION

Sample preparation is an important part of many biological methods and is exceedingly important in situations where the biological sample is uncharacterized. In such situations there is a need for a universal method for extracting nucleic acids from a variety of bacterial cell and spores.

Sample preparation is also an important part of biotechnology, including microarray (biochip, microchip) technology. DNA microarray protocols require random fragmentation and fluorescent labeling of target nucleic acids prior to hybridization. Sequence-independent fragmentation is necessary to reduce the size of the nucleic acids and minimize three-dimensional structure in the target region, making the target more accessible for on-chip hybridization. Fragmentation also allows different regions of a target molecule to independently interact with immobilized oligonucleotide probes.

Recently a Standard Protocol (S-Protocol) was developed for a single-tube and minicolumn format of nucleic acid isolation, fragmentation and labeling (U.S. Pat. No. 6,818,398 B2). The S-Protocol is based on radical-generating coordinating complexes chemistry (U.S. Pat. No. 7,208,269 B2), which is hereby incorporated by reference in its entirety. The S-Protocol was also configured for manual operation in the field (i.e. as a syringe-operated column), mobile, or stationary laboratory environment, and the extraction and analysis of nucleic acids from Gram positive and Gram negative vegetative bacteria. The protocol was validated for both DNA and RNA targets and was published (Bavykin et al., 2001, Appl. Environm. Microbiol. 67, 922-928; Kelly et al., 2002, Analyt. Biochem. 311, 103-118). One drawback to S-Protocol is that the lysis conditions are ineffective on spores or other recalcitrant organisms.

Several protocols have developed for extracting nucleic acids from spores and other recalcitrant organisms, however, these prior art techniques are inadequate for high yield of nucleic acids from such organisms because they focus on spore disruption techniques that only partially degrade or crack the outer membranes of the organism's complex system of cellular walls (i.e. spore). Many of these prior art methods tend to focus on physical disruption techniques such as sonication, glass bead mixing etc., heat shock treatment, taking advantage of germination (spore sprouting) and/or combinations thereof to disrupt the spore wall structure and release nucleic acids, followed by known extraction techniques to extract the released nucleic acids. As a result, many prior art techniques tend to release only extracellular nucleic acids that often exists in the spore samples as a result of incomplete spore purification from parental cells and fail to achieve high nucleic acid yields, which require extraction of intracellular nucleic acids. Furthermore, prior art protocols focus almost entirely on extraction from spores and are not appropriate for extraction of multiple cell types. While prior art methods may produce enough nucleic acid yield for PCR, such method do not typically produce adequate amounts of nucleic acid for direct analysis.

One method for extracting nucleic acids from spores is described by Moeller et al., "A Method for Extracting RNA from Dormant and Germinating *Bacillus subtilis* Strain 168 Endospores," Current Microbiology Vol. 53, (2006), pp 227-231, herein referred to as "Moeller." Moeller examined the extraction of nucleic acids from coated and decoated spores by germination (incubation times between of up to 120 minutes) followed by a acid-phenol extraction method. Therefore, Moeller's method actually represents protocol of nucleic acids extraction from vegetative cells, not from spores. Several prior art extraction methods also employ a germination/extraction approach including: Luna et al., "Novel Sample Preparation Method for Safe and Rapid Detection of *Bacillus anthracis* Spores in Environmental Powders and Nasal Swabs, Journal of Clinical Microbiology, March 2003, 1252-1255, which combines sonication, autoclaving and germination to extract nucleic acids from spores. However, all of these methods may not be considered as genuine methods of nucleic acids isolation from dormant spores. In all of these methods dormant spores were converted in growing cells before the beginning of nucleic acids isolation.

Kuske et al., "Small Scale DNA Sample Preparation Method for Field PCR Detection of Microbial Cells and Spores in Soil," Applied and Environmental Microbiology, July 1998, 2463-2472, describes another typical spore extraction method combining the use of heat treatment, freeze-thaw cycles, and bead mill homogenization. While the Kuske method provides limited amounts of nucleic acids the yield is low which is typical of most prior art methods. Furthermore, the harsh conditions used by Kuske are not acceptable for most vegetative cells. See, also Van Assche et al., "The Pattern of Protein and Nucleic Acid Synthesis in Germinating Spores of *Phycomyces blakesleeanus*," Arch. Mikrobiol. 93, 129-136 (1973), which combines heat shock with chemical disruption; Belgrader et al., "A Minisonicator to Rapidly Disrupt Bacterial Spores for DNA analysis," Anal. Chem. 1999, 71, 4232-4236, which combines sonication and germination to achieve spore disruption; and Chandler et al., "Continuous Spore Disruption Using Rapidly Focused, High-Frequency Ultrasound," Anal Chem. 2001, 73, 3784-3789, which employs high-frequency ultrasonication to achieve spore disruption.

Sargent et al., "A Procedure for Isolating High Quality DNA from Spores of *Bacillus subtilis* 168," Journal of General Microbiology (1980), 116, 511-514, describes a complex method for isolating DNA from *Bacillus* spores. While the Sargent procedure produces a good yield (80%) it is very time-intensive (~16 hours), is not suitable for use on a column due to the use of urea (and/or phenol), which tend to clog silica columns, and like most other spore extraction techniques is not suitable for use in mixture of multiple cell types like mixtures vegetative bacterial cells and bacterial spores. Other similar methods are disclosed by Papaphilis et al., "Defined conditions for DNA Extraction from *Bacillus subtilis* Spores," Biochiim, Biohpys. Acta, 199 (1970) 548-550;

and Dose et al., "DNA Stability and Survival of *Bacillus Subtilis* Spores in Extreme Dryness.

Given the limitation of prior art methods there exists a need for an effective, time-efficient method for extracting nucleic acids from a complex biological sample which is applicable for mixture of multiple types of cell including but not limited to: prokaryotic or eukaryotic cells and spores. The method would preferably be an on column method which could be easily automated and/or used in the field. Such a method would be especially useful for extracting nucleic acids from uncharacterized samples.

BRIEF SUMMARY OF THE INVENTION

The present invention relates to a method for extracting nucleic acids from biological samples. More specifically the invention relates to a universal method for extracting nucleic acids from unidentified bacterial samples. An advantage of the presently invented method is its ability to effectively and efficiently extract nucleic acids from a variety of different cell types and their mixtures, including but not limited to prokaryotic and eukaryotic cells and recalcitrant organisms (i.e. spores). Unlike prior art methods which are focused on extracting nucleic acids from cell or spores, the present invention effectively extracts nucleic acids from multiple cell types, spores and their mixtures is compatible with following microarray sample preparation (nucleic acid labeling, fragmentation and purification) using a single centrifuge minicolumn containing Silica, which is simple for automation. For standard laboratory environment, protocol also may be performed in common 1.5-2.5 ml microcentrifuge tubes. Important that the invented method has demonstrated an ability to extract nucleic acids from spores and vegetative bacterial cells with similar levels effectiveness. The invented method employs a multi-step protocol which erodes the cell structure of the biological sample. Specifically the method uses a first protease treatment, followed by a lysozyme treatment, followed by a second protease treatment, followed by a final lysis step. This multi-step procedure is necessary to erode the complex cell wall structure of recalcitrant organisms. However, the method also employs a recapture procedure to recover nucleic acids that may be released at various stages of the procedure. For example, the cell structure of Gram negative bacteria may be almost completely destroyed after the first protein treatment. Therefore the recovery steps are a salient aspect of at least one preferred embodiment to ensure the recapture of nucleic acids release in the various treatment stages.

The invented Universal method generally comprises: a first protease treatment, a first lysozyme treatment, a second protease treatment a final lysis step. The method can be continued with nucleic acid labeling, fragmentation and purification from the excess of the dye. The invented method is preferably performed on a column to allow easier automation. However, in laboratory environment, protocol may be easy performed in batch format with using centrifuge (microcentrifuge) tubes (i.e. one example is when Silica is applied in standard 1.5-2.5 ml microfuge tubes).

One preferred embodiment of the invention generally comprises the following steps:
  providing a biological sample containing vegetative bacterial cells or bacterial spores, or their mixtures;
  applying the biological sample to a column;
  performing a first protease treatment on the column;
  performing a first lysozyme treatment on the column;
  performing a second protease treatment on the column;
  performing recapturing procedure;
  performing lysis on the column with a lysis buffer (without $Mg^{2+}$ ions);
  adding a $Mg^{2+}$ containing compound/mixture to the column to bind the nucleic acid to the silica column. This entire process typically takes between about 30 and 60 minutes. Elution of the immobilized nucleic acids can be performed at this stage or after subsequent processing (i.e. labeling etc.).

One preferred embodiment the method further comprises the steps of fragmenting, labeling and purification of the immobilized genetic material (DNA or/and RNA) and eluting the labeled material from the column. One exemplary method fragmenting, labeling, purification and eluting the material can be found in U.S. Pat. Nos. 6,818,398 and 7,208,269 for more details, which are hereby incorporated by reference in its entirety. The entire process from beginning of the extraction and completing by elution of the pure labeled-fragmented sample typically takes less than about 2 hours, and generally between about 1-2 hours.

The invented Universal method works well for both spores and vegetative (Gram positive and Gram negative) cells, and the inventors have demonstrated effective equivalency between the Universal Protocol (U-Protocol) and S-Protocol.

BRIEF DESCRIPTION OF THE DRAWINGS

FIG. 1—illustrates the average absolute signal at each probe after microarray hybridization with *B. thuringiensis* ssp. *subtoxicus* H6 fluorescently labeled nucleic acids and standard error, calculated as the average signal intensity for each probe minus average background. The probe order is the same for all three charts, which contain microarray probes, as well as empty spots used for background calculation.

FIG. 2—shows average absolute signal for the entire biochip, calculated as in FIG. 1 but over all probes.

FIG. 3—illustrates absolute signal to background and standard error, calculated as the (average signal intensity for reach probe minus average background)/average background. The probe order is the same for all three charts (for details, see FIG. 1).

FIG. 4—shows average absolute signal: background for the entire biochip, calculated as in FIG. 3 but over all probes.

FIG. 5—illustrates subgroup recognition values, which are the ratios of fluorescent signals from perfectly matched (PM) and mismatched (mm) probes of specific probe pairs. Recognition values were obtained for all samples, arrays and probe pairs using customized software "Microchip Reader" (Copyright: TXu 1-026-755) developed for subgroup recognition in *Bacillus cereus* group. Only probe pairs used for specific subgroup recognition are shown. Chips used in this study effectively recognized all subgroups for signals that were only 20% higher than background.

FIG. 6—illustrates average subgroup recognition values for all samples and arrays.

FIG. 7—shows total nucleic acid yield and summary statistics for all other samples.

FIG. 8—is a statistical treatment of hybridization signals and backgrounds to estimate method sensitivity FIG. 9—is a table of recognition values for each sample extract and biochip

DETAILED DESCRIPTION OF THE PREFERRED EMBODIMENT

The present invention relates to a method for extracting nucleic acids from bacterial sample(s) containing vegetative bacterial cells or/and bacterial spores. More specifically one embodiment of the invention relates to a universal method for extracting nucleic acids from bacterial samples containing any, Gram positive or Gram negative bacterial cells, spores, or their mixtures. An advantage of the presently invented method is its ability to effectively extract nucleic acids from a variety of different cell types including but not limited to vegetative cells and spores.

Figure 2:
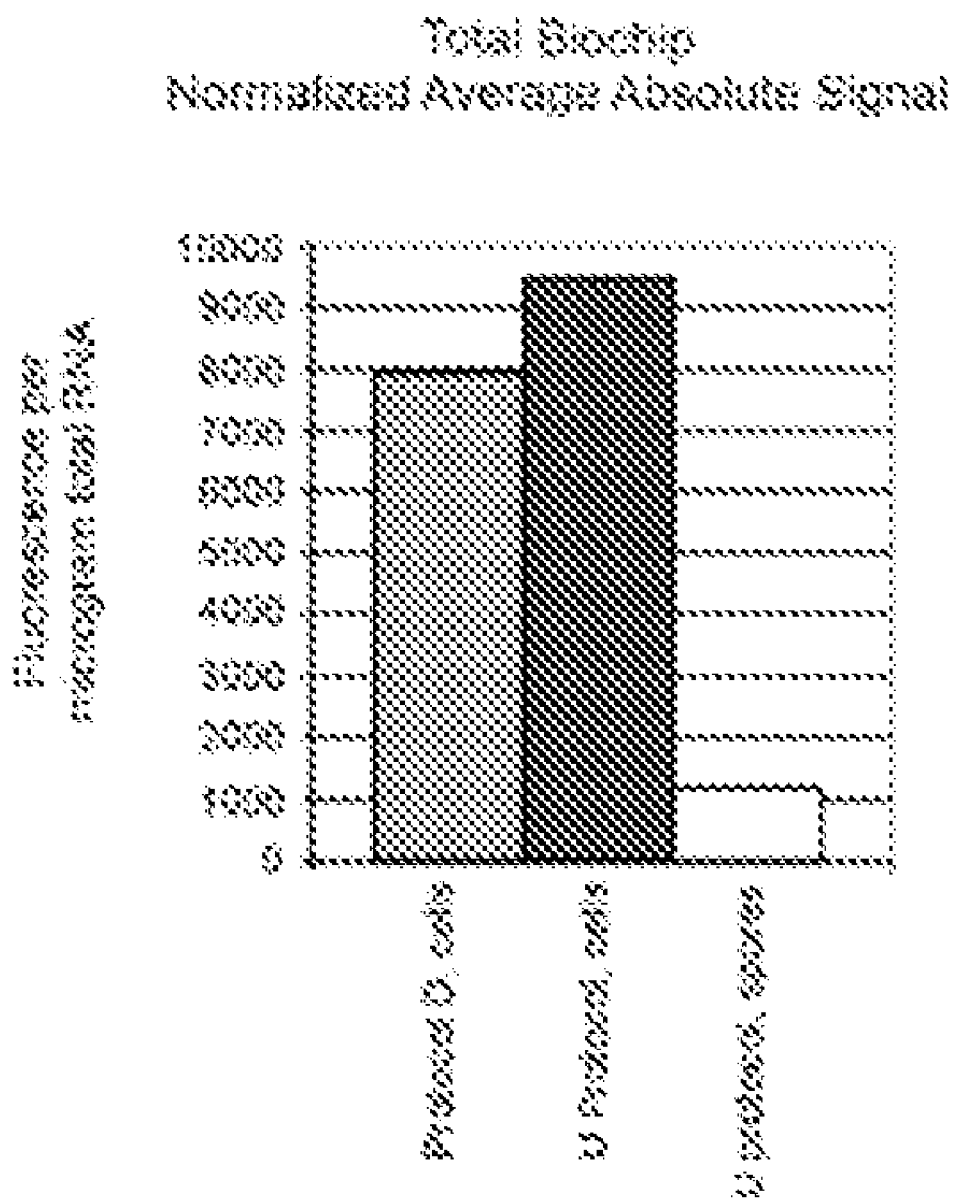

1. Universal Method for Nucleic Acids Extraction

The invented Universal method generally comprises: a first protease treatment, a first lysozyme treatment, a second protease treatment, recapturing procedure and a lysis step. The invented method is preferably performed on a column to allow easier automation.

One preferred embodiment of the invention generally comprises the following steps: providing a biological sample containing unidentified bacterial cells or/and spores, or their mixtures; applying the biological sample to a column; performing a first protease treatment on the column; performing a lysozyme treatment on the column; performing a second protease treatment on the column; performing recapturing procedure, applying the column the with a lysis buffer (without $Mg^{2+}$ ions) to perform complete lysis of the pretreated cells and spores on the column and release nucleic acids; adding a $Mg^{2+}$ containing compound/mixture to the column to bind the nucleic acid to the Silica column. Elution of the DNA or/and RNA can be performed at this stage or after labeling, or other additional steps.

Although the invented method is preferably performed on-column to allow easier use in the field, the method can also be performed by replacing the Silica column with centrifugation tubes filled with a suitable material (i.e. Silica), wherein the procedures are performed in a batch format repeating all steps of column procedure.

It may be possible to use the method on viruses, fungi, plants and other organisms, although, various modifications may be necessary.

1.1. Providing Biological Samples

Preferably the sample is suspended in a solution (i.e. water) before application to the column. The maximum number of organisms that can be applied to the Universal Silica Minicolumn is about $5 \times 10^8$ cells or about $5 \times 10^9$ spores per sample. The maximum sample volume is about 250 microliters per column.

1.2. Affinity Column

Although the column is preferably a Silica minicolumn described in detail below, other columns may be employed. A variety of column shapes, diameters and lengths are suitable. A myriad of packing materials are suitable column constituents including but not limited to: Silica, ground glass filter, pulped glass filter, $HNO_3$-washed glass filter pulp, $HNO_3$-washed gel, $HNO_3$-washed diatoms, Silica acid 400 mesh silica gel, SPE-SIL, Silica beads, and combinations thereof.

A syringe-type column can be employed to replace the centrifugation steps. A suitable syringe-type column and method is described in U.S. Pat. No. 6,818,398 issued to Bavykin et al., which is hereby incorporated by reference in its entirety.

In an alternate embodiment the Silica column could be replaced with one or more affinity matrices including but not limited to affinity beads, affinity gels, affinity resins, affinity plates, and combinations thereof.

1.3. Applying Biological Sample to a Column

The uncharacterized biological sample can be applied to a column in a variety of ways including but not limited to pouring, pipeting etc. Upon application of the sample the column the Silica in the column should be resuspended. Resuspension can be accomplished in a number of ways including but not limited to vigorous pipetting, magnetic beads/rods stirring, gas bubbling etc. Microorganisms are preferably applied to the Silica column at slightly acidic pH rather than at neutral pH. The acidic pH dramatically improves buffer filtration through the column during all stages of pretreatment, which was a significant problem during the manipulation of spores. A suitable slightly acidic pH is between about 2 and 4.

1.4. First Protease Treatment

The first protease treatment is a salient part of the invented invention as allows begins to breakdown the spore coat layer structure. The amount of cell wall degradation on this stage caused by the first protease treatment largely depends on the type of cell(s) (Gram negative, Gram positive, spore etc.) present in the biological sample. For example, the first protease treatment may be sufficient to destroy all or nearly all of the cell wall structure of Gram negative cells while the first treatment may only partial disrupt Gram positive, spores and other hardier cell types.

A first protease containing mixture is applied to the column and allowed to incubate. Incubation times can be varied. Suitable incubation times are between about 1 min and 10 min, preferably about 5 min. Shorter or longer incubation periods can be employed according to conditions and desired results. After incubation, the column is preferably centrifuged.

Since the first protease treatment can destroy nearly the entire cell wall structure of Gram-negative cells, the flow though should be stored as it may contain nucleic acids released by Gram-negative cells. Any nucleic acid present in the flow-through can then be recovered using a recovery stage as described later.

After centrifugation, the column is washed with a washing solution to remove any excess protease. Although the washing solution can be water in the case of spore treatment, however to avoid osmotic lysis of other cells that may present in mixed sample, it was found that an alcohol solution is preferred. More preferably the washing solution is an ethanol solution, even more preferably a 75% ethanol solution. After washing, the column is preferably centrifuged. The washing and centrifugation steps can be repeated when desirous.

As discussed in detail below, the first protease treatment employs a protease. While many proteolytic enzymes may be used, Pronase, subtilysin, etc., the preferred protease is Proteinase K because it's high activity and good solubility in 75% ethanol, which is using as a washing solution after protease treatments. While many protease buffers could be employed it was found that using a buffer without SDS dramatically increased Silica aggregation on the column and improves filtration speed through the column.

1.5. Lysozyme Treatment

The lysozyme treatment is a salient part of the invented invention as allows continues the breakdown of the polysaccharide of peptidoglycans representing a main component of cortex (internal part of spore wall that is situated under the coat layers) and external part of the Gram positive cell wall. The amount of cell wall degradation caused by the lysozyme again largely depends on the type of cell(s) (Gram negative, Gram positive, spore etc.) present in the biological sample. For example, the first protease treatment may be sufficient to destroy or nearly destroy the entire cell wall structure of Gram negative and Gram positive cells, while the lysozyme treatment may only partial disrupt spores and other hardier cell types.

A lysozyme containing mixture is applied to the column and allowed to incubate. Incubation times can be varied. Suitable incubation times are between about 1 min and 10 min, preferably about 5 min. Shorter or longer incubation periods can be employed according to conditions and desired results. After incubation the column is preferably centrifuged. Since the combination of the first protease treatment and first lysozyme treatment can destroy nearly the entire cell wall structure of Gram negative and Gram positive cells, the flow though should be stored as it may contain nucleic acids released by such cells. Nucleic acids present in the flow-through can be recovered later using a recovery stage as described below.

After centrifugation, the column is washed with a washing solution to remove any excess lysozyme. Like the washing solution can be water in the case of pure spore washing, but working with unknown cells on the stage of first protease treatment an alcohol solution was preferred. More preferably the washing solution is an ethanol solution, even more preferably about a 75% ethanol solution. After washing, the column is preferably centrifuged. The washing and centrifugation steps can be repeated when desirous.

1.6. Second Protease Treatment

The second protease treatment is a salient part of the invented invention as allows continues to breakdown the biological sample's wall structure. The amount of cell wall degradation caused by the second protease treatment largely depends on the type of cell(s) (Gram negative, Gram positive, spore etc.) present in the biological sample. For example, the second protease treatment may be sufficient to destroy all or nearly all of the cell wall structure of Gram negative cells, the second protease treatment may only partial disrupt Gram positive, spores and other hardier cell types. Specifically in the case of spores, second protease treatment targets cortex protein disruption.

A second protease containing mixture is applied to the column and allowed to incubate. Incubation times can be varied. Suitable incubation times are between about 1 min and 10 min, preferably about 5 min, although times can vary depending upon conditions and/or desired results. After incubation the column is preferably centrifuged. Since the second protease treatment can destroy nearly the entire cell wall structure of Gram positive cells (which becomes protease-sensitive after lysozime treatment), the flow though should be stored as it may contain nucleic acids released by Gram positive cells. Any nucleic acid present in the flow-through can then be recovered using a recovery stage as described later.

The second protease treatment employs a protease as discussed above in regard to the first protease treatment. The preferred protease is Proteinase K.

1.7. Final Cell Lysis

Although the protease and lysosyme treatments completely destroy Gram negative and Gram positive cells, the more recalcitrant organism (i.e. spores) require a final lysing treatment which results in a high yield about 80-100% (yield for spores). It is very important to note that the presence of Mg2+ in the final lysis step stabilizes the spheroplast cell walls and decreases lysis efficiency dramatically (to about 10-20%). Therefore Lysis-Binding buffer (also referred to herein as LB buffer, L:B buffer and Lysis Buffer:Binding Buffer) without MgCl2, should be used in the final lysing step. Removal of Magnesium ions that stabilize cell membranes from the LB buffer for spheroplast disruption dramatically increased (5-10 times) spore lysis efficiency.

However, since $Mg^{2+}$ ions are necessary for binding nucleic acids to Silica, a magnesium containing compound/solution should be added to the Silica after treating the column with LB buffer.

1.8. Recovery of Nucleic Acids Released at Various Stages of the Pretreatment Process This is an important part of the invention as it allows for the recovery of nucleic acids that have been released at the various stages of the pretreatment process. Recovery is achieved by applying the various saved flow-throughs (singularly or in combined formed) to the column wherein the nucleic acid present in the flow-throughs are also immobilized onto the column. Alternatively and preferably, the ethanol-precipitated flow-throughs obtained on stages 1.4-1.6. should be applied on the column between the Second Protease Treatment (stage 1.6) and Final Cell Lysis (stage 1.7.).

1.9. Nucleic Acids Purification and Elution

After nucleic acids immobilization, the column is washed consequently with LB buffer to remove cell debris and with ethanol to remove traces of LB buffer. More preferably ethanol treatment should be performed twice with 75% ethanol and the twice with 100% ethanol. Following the purification, the nucleic acid can be eluted from the column using a variety of techniques known in the art including but not limited to the technique described in detail below One preferred method of elution generally comprises adding sodium carbonate to the column followed by insertion of the column in a heat block (i.e. 95° C.) for a few minutes, followed by centrifugation, wherein the nucleic add is then present in the flow-through. These steps can be repeated to increase yield as desired.

Alternatively, elution can be performed after subsequent labeling or other post extraction processes as described below.

1.10. Centrifugation and Alternatives

Typical sedimentary forces and times are employed to effect separation of target from non-target moieties in the present invention. Centrifugation at about 10,000-14,000 g for between about 30 second and 5 minutes produces good results, although speeds and times can be varied as necessary or according to conditions and/or results.

Centrifugation used in the present invention can be replaced by employing the use of syringe type columns as described in detail in U.S. Pat. No. 6,818,398, which is hereby incorporated by reference in its entirety. As a variant, gas pressure or vacuum may be used for solution exchange in the column as an alternative to column centrifugation.

2. Exemplary Protocols

One preferred embodiment of the invention relates to a method for extracting nucleic acids from a biological sample comprising: providing a biological sample containing unidentified nucleic acids; applying the biological sample to a column; treating the column with a first protease containing mixture and allowing the treated column to incubate; centrifuging the column and collecting the flow-through forming a first collected flow-through precipitated with ethanol; washing the column with a first alcohol solution; centrifuging the column and discarding the flow-through, treating the column with a lysozyme containing mixture; centrifuging the column, collecting the flow-through forming a second collected flow-through precipitated with ethanol; washing the column with a second alcohol solution; centrifuging the and discarding the flow-through, treating the column with at second protease containing mixture; centrifuging the column, collecting the flow-through forming a third collected flow-through precipitated with ethanol; applying all three ethanol-precipitated flow-throughs to the column to recover nucleic acids lost on previous stages; applying the column with a first magnesium free LB buffer without $Mg^{2+}$ (i.e. without $MgCl_2$) to lyse remaining cells and release their remaining nucleic acids.

Finally, a $MgCl_2$ containing solution (or other $Mg^{2+}$ containing solution) is added to the column to bind the released nucleic acids to the column. Immobilized nucleic acids is washing consequently with lysis buffer to remove debris and with ethanol to wash out lysis buffer.

2.1. Preparation

The following materials and reagents should be assembled and organized in the workspace before beginning any other Procedure (Table 1).

microliters water. Add 90 microliters of β-mercaptoethanol (E1 solution). Diluted Proteinase K solution may be stored at −20° C. for up to one week.

Dissolve Lysozyme in water to a final concentration 100 mg/ml (E2 solution) and store at 4° C. or on ice. Lysozyme is preferably prepared fresh. Sodium phosphate pH 6.4 was eliminated from Lysozyme buffer, which makes it possible to ethanol precipitate the flow-through and recover free nucleic acids (phosphate is insoluble in presence of high concentrations of ethanol and precipitates irreversibly).

2.1.4. Ethanol Preparation

To prepare 0.4 M sodium acetate in 96% ethanol (EtOH-Ac solution), mix 3.28 g of sodium acetate in 96 milliliters of 100% ethanol, add 4 milliliters of water, add a stir bar, and

TABLE 1

| Chemicals and Solutions | Materials |
|---|---|
| Silica suspension | VectaSpin Anapore ™ 0.2 μcentrifuge filter unit |
| DEPC-treated $H_2O$ | 1.5 ml microfuge tubes |
| LB buffer w/o $MgCl_2$ | Pipettors |
| 4.9 M $MgCl_2$ | Water bath |
| $CuSO_4$ $5H_2O$ | Disposable pipette tips |
| o-phenanthroline —HCl monohydrate | Glass beads-filled heat block |
| 1 milligram ampules of Lissamine Rhodamine | Eppendorf Centrifuge 5415C |
| Proteinase K | |
| Lysozyme | |
| 30% $H_2O_2$ | |
| 100% Ethanol | |
| 75% Ethanol | |
| 25 mM sodium phosphate buffer, pH 7.0 | |
| β-mercaptoethanol | |
| Elution Buffer | |

Turn glass beads-filled heat block on and pre-warm to 95° C. at least two hours prior to the experiment to stabilize temperature.

A single Silica minicolumn will be used for cell or spore concentration and lysis, and nucleic acid isolation, labeling, fragmentation and purification. It was found preferably to keep the Silica and water solution in a ratio of about 1 part 0.1 N HCl to 2 parts Silica in stock Silica suspension.

2.1.1. Silica Minicolumn Preparation

Add enough Silica stock suspension to a VectaSpin Anapore™ 0.2μ centrifuge filter unit to result in a 40 microliters Silica in column. Centrifuge filter unit at 14,000 rpm (14,000×g) for 2 min, and discard the flow-through from the retention tube.

It is important to not wash the Silica with water or any other solution before applying the unknown or uncharacterized sample. The Silica suspension is stored at acidic pH, which is necessary for spore absorption onto the Silica particles and all subsequent manipulations for spore disruption. Spores that are not absorbed to the Silica will form a film on the top of the column during centrifugation, which will prevent solutions from filtering through the column.

2.1.2. LB Buffer Activation (Activated LB Buffer)

Mix 19.5 ml of LB buffer and 263 μl of 4.9M $MgCl_2$. Keep at room temperature. Activated LB buffer is stable for up to 7 days.

2.1.3. Enzymes Preparation

Dissolve Proteinase K in water to achieve a final concentration 40 mg/ml. If necessary, warm the solution up to 35-45° C. to dissolve enzyme completely. Place 450 microliters of 40 mg/ml Proteinase K solution into a fresh tube. Add 360 dissolve the sodium acetate by stirring and heating the solution to 30-40° C. The solution can be stored for up to 12 months with the stir bar inside the flask. Heating the solution to 40° C. should redissolve small amounts of sodium acetate crystals that appear during storage. Do not filter the solution in order to remove crystals. Prepare tree microfuge 1.5 ml tubes containing 300 microliters of EtOH-Ac each.

2.1.5. Biological Sample Preparation

Uncharacterized samples containing suspected cells or spores should be reconstituted and suspended in 250 microliters of water. The use any buffers or cell growth mediums to resuspend cells or spores should be avoided, as these solutions will change the pH of the Silica surface during perfusion and prevent proper interaction of spores and Silica.

Preferably, the sample volume should not exceed about 250 microliters. Applying larger volumes of sample (or water) to the column will also disrupt the pH of the Silica surface.

It is important not resuspend samples or Silica/sample pellet in acidified water, as nucleic acids may degrade before being captured on the Silica.

2.2. Lysis and Nucleic Acid Purification

The following protocol may be used for spores, Gram positive and Gram negative vegetative cells disruption and isolated nucleic acids purification.

TABLE 2

| Chemicals & Solutions | Materials |
|---|---|
| β-mercaptoethanol | 1.5 milliliter microfuge tubes |
| Proteinase K | Disposable pipette tips |

TABLE 2-continued

| Chemicals & Solutions | Materials |
| --- | --- |
| Lysozyme | Silica Minicolumns |
| DEPC-treated H$_2$O | Pipettors |
| Activated LB buffer | Eppendorf Centrifuge 5415C |
| LB buffer w/o MgCl$_2$ | |
| 100% ethanol | |
| 75% ethanol | |
| 0.4 M sodium acetate in 96% ethanol | |

Apply the uncharacterized cell/spore sample (in 250 microliters of water) to the column. Carefully suspend the Silica via gentle pipetting action. Preferably use wide-bore pipette tips for this step. Centrifuge column for 1 min at 14,000×rpm and discard the flow-through.

2.2.1. First E1-Treatment (First Protease Treatment):

Add 100 microliters of E1 into the column and resuspend Silica by gentle pipetting. Incubate 5 min at room temperature. Centrifuge 2 min at 14,000×rpm, collect the flow-through and transfer it to a first microfuge tube containing 300 microliters of EtOH-Ac solution. The E1 flow-through may contain nucleic acids released from broken Gram negative cells. Vortex the E1/ethanol mixture briefly and keep it at room temperature.

2.2.2. Ethanol Washing (Alcohol Treatment):

Add 100 microliters of 75% ethanol into the column and resuspend Silica by gentle pipetting. Centrifuge 2 min at 14,000×rpm and discard the flow-through. Repeat the ethanol wash once.

2.2.3. E2-Treatment (Lysosyme Treatment):

Add 100 microliters of E2 into the column and resuspend Silica by gentle pipetting. Incubate 5 min at room temperature. Centrifuge 2 min at 14,000×rpm, collect flow-through and transfer it into a second microfuge tube containing 300 microliters of EtOH-Ac solution. The E2 flow-through may contain nucleic acids released from broken Gram positive cells. Vortex mixture E2/ethanol mixture briefly and keep it at room temperature.

2.2.4. Ethanol Washing (Alcohol Treatment):

Add 100 microliters of 75% ethanol into the column and resuspend Silica by gentle pipetting. Centrifuge 2 min at 14,000×rpm and discard the flow-through. Repeat the ethanol wash once.

2.2.5. Second E1-Treatment (Second Protease Treatment)

Add 100 microliters of E1 into the column and resuspend by gentle pipetting. Incubate 5 min at room temperature. Centrifuge 2 min at 14,000×rpm, collect the flow-through and transfer it into a third microfuge tube containing 300 microliters of EtOH-Ac solution. The flow-through after the second E1 treatment may contain nucleic acids released from broken spores. Vortex second E1/ethanol mixture briefly and keep it at room temperature.

2.2.6. Final Lysis and Binding of Released Nucleic Acids to Silica:

Proteinase K and Lysozyme treatments completely destroy Gram negative cells, but are not 100% effective on spores and Gram positive cells. The remaining spherolasts can be lysed with 80-100% yield in LB buffer without Mg$^{2+}$.

Lysis of remaining spheroplasts in this buffer makes buffer filtration through the Silica minicolumn quite difficult at this stage. To increase nucleic acid yield, the Silica resin and cell pellet should be vigorously and completely re-suspended to break up as many remaining cells and spores as possible. Avoid touching the filter with the pipette tip to avoid damage of the filter.

Add 150 microliters of LB buffer without MgCl$_2$ to the Silica column. Resuspend vigorously (wide-bore pipette tips are best suited for this step). Add 3.4 microliters of 4.9 M MgCl$_2$ to the Silica. Centrifuge 3 times for 2 min each at 14,000×rpm, rotating the column 180° after the first centrifugation and 90° after the second centrifugation to provide complete filtration. Some liquid may stay in the column after the third centrifugation. If the residual volume does not exceed 50 microliters, proceed to the next stage. Otherwise, repeat centrifugation until the residual liquid volume over the top of the Silica is less than 50 microliters.

2.2.7. Recovery of Nucleic Acids Released During Pretreatment

The purpose of this step is to recover nucleic acids that may have been released during the initial spore and cell lysis steps.

Apply the first E1/ethanol flow-throw mixture (~400 microliters) into the column and resuspend Silica. Centrifuge 2×2 minutes, rotating the column 180° after the first centrifugation. Apply the E2/ethanol and second E1/ethanol flow-throw mixtures onto the column in the same manner.

Alternatively, the first E1, E2, and second E1 flow-through mixtures can be combined before application to the column. Alternatively and preferably, recovery of nucleic acids released during pretreatment (stages 2.2.1.-2.2.5.), may be performed between stages 2.2.5. and 2.2.6.

2.2.8. LB Buffer Washing

Washing of minicolumn with activated LB buffer removes debris remained on the column after cell disruption and traces of enzymes (particularly lysozyme) that have a tendency to co-precipitate with nucleic acids during ethanol precipitation.

Apply 150 microliters of activated LB buffer into the column and re-suspend Silica. Centrifuge 2×2 minutes, rotating the column 180° after the first centrifugation. If the buffer has not completely passed through the Silica column after the second centrifugation, remove remaining buffer from above the Silica using a pipette and discard it. Subsequent ethanol washes will flush the rest of the LB buffer through the Silica and increase the ease with which solutions are filtered.

2.2.9. Ethanol Washing

Add 250 microliters of 75% ethanol into the column and resuspend Silica by gentle pipetting. Centrifuge for 1 min at 14,000×rpm and discard flow-through.

Repeat the 75% ethanol wash once. Add 250 microliters of 100% ethanol to the column, but do not resuspend the Silica. Centrifuge for 1 min at 14,000×rpm and discard flow-through. Repeat the 100% ethanol wash once.

2.3. Nucleic Acid Labeling and Fragmentation

Following pretreatment the nucleic acids immobilized on the column can be labeled, fragmented (see Solutions and Material in Table 3) and subsequently used for hybridization analysis, particularly with DNA microarray, preferably with DNA microarray bearing oligonucleotide probes.

TABLE 3

| Solutions | Materials |
| --- | --- |
| 25 mM sodium phosphate pH 7.0 | Eppendorf Centrifuge 5415C |
| DEPC-treated water | 1.5 milliliter microfuge tubes |
| 30% H$_2$O$_2$ | Pipettor |
| 3 M sodium acetate pH 7.0 | Disposable pipette tips |
| 0.5 M Na$_2$EDTA pH 8.0 | Timer |

TABLE 3-continued

| Solutions | Materials |
|---|---|
| Pre-weighed CuSO$_4$ 5H$_2$O | Glass beads-filled heat block |
| Pre-weighed o-phenanthroline —HCl | |
| Lissamine rhodamine B ethylenediamine, 1 mg ampules | |
| Caps for standard 1.5 ml microcentrifuge tubes | |

Dissolve CuSO$_4$5H$_2$O and o-phenanthroline-HCl in DEPC-treated water to achieve a concentration of 3.76 mg/ml and 35.2 mg/ml, respectively.

The most common mistake at the stage of labeling cocktail preparation is accidentally adding water to the Lissamine Rhodamine instead of sodium phosphate. Substituting water for sodium phosphate will decrease labeling efficiency approximately 50-fold. Add 1210 microliters of 25 mM sodium phosphate pH 7.0 solution to the ampule of 1 milligram Lissamine Rhodamine dye. Mix the solution vigorously for 1 min. Not all of the ampule contents will dissolve into solution. The insoluble material is mostly dye carrier. However, if the carrier crystals are carried into the Silica column, residual dye in the insoluble crystals will increase biochip image background and therefore lead to inconsistent bacterial recognition. It is therefore important to remove insoluble particles from the dye solution before applying the dye to the Silica minicolumn. Centrifuge the dissolved dye for 1 min at 14,000×rpm.

Collect 732 microliters of supernatant and transfer to a new tube, being careful to avoid the insoluble pellet. Add 30 microliters of dissolved CuSO$_4$ to the 732 microliters of dye. Finally, add 30 microliters of dissolved o-phenanthroline-HCl into the same tube. Vortex briefly. Remove 132 microliter portions of the labeling cocktail into each of four separate 1.5 ml microfuge tubes.

Prepare the 133.3 mM hydrogen peroxide solution: combine 975 microliters of DEPC-treated water and 15 microliters of 30% H$_2$O$_2$. Prepare the Stop Buffer. Combine 86.5 microliters of 3 M sodium acetate (pH 7.0) and 13.5 microliters of 0.5 M EDTA (pH 8.0). Set digital timer to 0:00 and begin the staged reactions for 4 minicolumns according to the timetable shown in Table 4. Each Silica minicolumn containing purified nucleic acids will be subject to the following manipulations. Remove column from the flow-through receptacle and seal bottom of the column with the cap from a 1.5 ml microfuge tube. Avoid crushing the AlO$_2$ membrane, and insert the seal only 1-2 mm. Incubate Silica minicolumn at 95° C. in a glass beads-filled heat block for 4 minutes with the top open. While the Silica minicolumn is incubating, preheat the labeling cocktail to 95° C. for 30 seconds.

Add 18 microliters of diluted H$_2$O$_2$ to the labeling cocktail while the tube is still in the 95° C. heat block. Transfer the entire volume of the pre-heated labeling cocktail to the preheated Silica minicolumn without removing any tubes from the heat block. Resuspend Silica by gentle pipetting action, close the top with a lid and incubate at 95° C. in the heat block for 10 minutes.

Remove the Silica minicolumn from the heat block. Stop the reaction by adding 20 microliters of stop solution and 510 microliters of cold (−20° C.) 100% ethanol. Resuspend the Silica and close the top of the column with the lid. Incubate the Silica minicolumn for 5-10 minutes at room temperature. Nucleic acids are now fragmented and labeled with Lissamine Rhodamine dye.

TABLE 4

Fragmentation and Labeling Sequence (for four samples)

| Time (min) | Put column at 95° C. for 4 min preheating with top open | Put tube with labeling cocktail at 95° C. for 30 sec preheating | Add 18 μl 133.3 mM H$_2$O$_2$ into the cocktail, transfer mix into column, close cap on the top | Stop Reaction* (add 20 μl of Stop solution and 510 μl of cold 100% EtOH) |
|---|---|---|---|---|
| 0' | Column #1 at 0' | | | |
| 2' | Column #2 at 2' | | | |
| | | Tube #1 at 3'40" | | |
| 4' | Column #3 at 4' | | Column #1 4'10"-4'40" | |
| | | Tube #2 at 5'40" | | |
| 6' | Column #4 at 6' | | Column #2 6'10"-6'40" | |
| | | Tube #3 at 7'40" | | |
| 8' | | | Column #3 8'10"-8'40" | |
| | | Tube #4 at 9'40" | | |
| 10' | | | Column #4 10'10"-10'40" | |
| 12' | | | | |
| 14' | | | | Column #1 14'40"-15' |
| 16' | | | | Column #2 16'40"-17' |
| 18' | | | | Column #3 18'40"-19' |
| 20' | | | | Column #4 20'40"-21' |

2.4. Sample Purification from the Excess of the Dye

Fragmented and labeled nucleic acids must be purified from free Lissamine Rhodamine dye (see Solutions and Materials in Table 5). Failure to remove unbound dye will increase background after hybridization, and lead to variable results and inconsistent bacterial recognition.

TABLE 5

| Solutions | Materials |
| --- | --- |
| 75% ethanol | Microcentrifuge |
| 100% ethanol | 1.5 milliliter microfuge tubes |
| | Pipettors |
| | Disposable pipette tips |
| | Eppendorf Centrifuge 5415C |

Remove top and bottom caps from the Silica minicolumn, and recover any droplets of solution from the caps with a pipette tip. Load residual droplets back onto the Silica particles. Centrifuge the column for 1 minute at 14,000×rpm at room temperature and discard the flow-through. Resuspend the Silica with 500 microliters of 75% ethanol. Carefully wash the inside walls of the Silica minicolumn to remove all traces of labeling cocktail. Centrifuge the column 1 min at 14,000×rpm at room temperature and discard the flow-through. If necessary, thoroughly wash the outside surface of the filter unit with 100% ethanol to remove traces of the dye, dry column with a napkins. Resuspend the Silica with 500 microliters of 100% ethanol. Centrifuge the column for 1 min at 14,000×rpm at room temperature and discard flow-through.

The flow-through should be clear to the eye, indicating that all free Lissamine Rhodamine has been removed from the Silica minicolumn. If there is a visible "pink" tint to the ethanol flow-through, repeat 100% ethanol washes until the flow-through is colorless. Two 100% ethanol washes are usually sufficient to eliminate all visible traces of free Lissamine Rhodamine dye from the Silica particles.

2.5. Nucleic Acids Elution (Elution Step/Elution Treatment)

Table 6 indicates necessitate solution and materials. Place the Silica minicolumn into a new 1.5 milliliter centrifuge tube. Add 45 microliters of 10 mM sodium carbonate, pH 8.5 buffer to the Silica and thoroughly resuspend by gentle pipetting action. Place combined Silica Minicolumn/1.5 ml centrifuge tube into a 95° C. heat block for 2 minutes (top cup should be on). Centrifuge column for 1 min at 14,000×rpm at room temperature. Keep the flow-through in the 1.5 ml microfuge tube. Transfer Silica minicolumn into a new 1.5 ml microfuge tube. Add 35 microliters of 10 mM sodium carbonate, pH 8.5 buffer to the Silica and thoroughly resuspend Silica by gentle pipetting action. Place combined Silica minicolumn/1.5 ml centrifuge tube into a 95° C. heat block for 2 minutes. Centrifuge Silica minicolumn for 1 minutes at 14,000×rpm at room temperature. Combine with the previous flow-through volume. The total volume should be approximately 70 microliters.

TABLE 6

| Solutions | Materials |
| --- | --- |
| 10 mM sodium carbonate, pH 8.5 | Eppendorf Centrifuge 5415C |
| | 1.5 milliliter microfuge tubes |
| | Pipettors |
| | Disposable pipette tips |

The purified, fragmented, labeled and eluted nucleic acid should have a clear or slightly pink tint, indicating that Lissamine Rhodamine dye was successfully coupled to the nucleic acid. The sample, average yield 20-50 microgram of total nucleic acids, is now ready for hybridization to the biochip. The average fragment size should be between 50-150 nucleotides.

If biochip hybridization will not occur immediately, then store the nucleic acid at −80° C. for up to one year.

The resulting size distribution of fragmented RNA is important for successful and reproducible hybridization results. The quality of fragmented and labeled nucleic acids (mostly comprising rRNA) may be analyzed using a small amount (~1 microgram) of eluted nucleic acid on a denaturing 7.5% polyacrylamide gel (AA:bisAA=19:1) with 7M urea.

APPENDIX A

Standard Suppliers for Materials and Reagents

Standardized Sources of Chemicals and Equipment

β-mercaptoethanol (Sigma-Aldrich, St. Louis, Mo., catalog #M-6250); cupric sulfate pentahydrate (Sigma-Aldrich, St. Louis, Mo., catalog #C7631); DEPC-treated water (Ambion, Foster City, Calif., catalog #9920); 0.5M EDTA, pH 8.0 (Ambion, Foster City, Calif., catalog #9260G); ethyl alcohol, absolute 200 proof, 99.5%, A.C.S. reagent (Sigma-Aldrich, St. Louis, Mo., catalog #45, 984-4);guanidine thiocyanate (Fisher, Waltham, Mass., catalog #BP221-1); 6 M guanidine thiocyanate (Fluka, St. Louis, Mo. catalog #50983); 30% w/w hydrogen peroxide (Sigma-Aldrich, St. Louis, Mo., catalog #H-1009); Lissamine rhodamine B ethylenediamine, 1 milligram ampules (Molecular Probes-Invitrogen, Carlsbad, Calif. catalog #L-2424). One milligram ampules are a custom package size; contact Molecular Probes directly at 1-800-438-2209; Lysozyme (Sigma, cat#L-7651; 50,000 activity units/microgram); 4.9 M magnesium chloride (Sigma-Aldrich, St. Louis, Mo., catalog #104-20); o-phenanthroline hydrochloride monohydrate (Fluka Chemical, catalog #77510); Proteinase K, 100 mg vial, 10-20 u/mg (Sigma-Aldrich, St. Louis, Mo., catalog #P-2308); Silica (Silicon dioxide, Sigma-Aldrich, St. Louis, Mo., catalog #S-5631); sodium bicarbonate (Fisher, Waltham, Mass., catalog #BP328-500); sodium phosphate, monobasic, anhydrous (Sigma-Aldrich, St. Louis, Mo., catalog #S8282); sodium phosphate, dibasic, anhydrous (Sigma-Aldrich, St. Louis, Mo., catalog #S7907); Triton X-100, reduced (Sigma-Aldrich, St. Louis, Mo., catalog #23, 210-3); 3M sodium acetate, pH7.0 (Sigma-Aldrich, St. Louis, Mo., catalog #S2404) 50% sodium hydroxide solution (Sigma-Aldrich, St. Louis, Mo., catalog #41,541-3); Tris, free base (Fisher, Waltham, Mass., catalog #BP154-1); Eppendorf Centrifuge 5415C (Fisher, Waltham, Mass., catalog #05-406-11), with fixed angle, 18-place, 1.5 ml tube rotor ($r_{average}$=65 mm). Extended pipette tips (BioRad, Hercules, Calif., catalog #223-9917); Kimwipes (Fisher, Waltham, Mass., catalog #06-666A); 0.5 ml microfuge tubes, siliconized, RNAse free (Ambion, Foster City, Calif., catalog #12350); Whatman VectaSpin Micro Anapore™, 0.2 μM centrifuge filter unit (Whatman, Middlesex, UK catalog #6830-020);

APPENDIX B

Reagent and Buffer Recipes

Preparation of Silica Particle Stock Solution

Silica particles are prepared according to the method of Boom et al. 1990, *J. Clin. Microbiol.* 28:495-503. The final Silica suspension should contain 40-60% Silica (v:v). Suspend 60 Grams of Silica particles in a graduated cylinder containing 500 milliliters of ultra-pure water. Allow the particles to sediment at unit gravity for 24 hours at room temperature. Remove 430 milliliters of the supernatant by gentle suction. Add ultra-pure water back to the graduated cylinder to achieve 500 milliliters total volume. Re-suspend the Silica particles by vigorous shaking. Allow the particles to sediment at unit gravity for 5 hours at room temperature. Discard 440 milliliters of the supernatant by gentle suction. Add 600 microliters of concentrated HCl (32% w/v) to adjust the suspension to pH 1. Full re-suspend the Silica particles by vigorous shaking. Divide suspended Silica particles into 4 milliliter portions, with each 4 milliliter portion placed in a small, dark glass bottle. Close the glass bottles and autoclave for 20 minutes at 121° C. to destroy any contaminating nucleic acid. Silica particles are stable for at least 1 year when stored at 4° C. in the dark.

25 mM Sodium Phosphate, pH 7.0

Weigh 3 grams sodium monophosphate ($NaH_2PO_4$) (Sigma, cat# S8282). Dilute in 400 milliliters of DEPC-treated water. Adjust volume to 500 milliliters. Filter through a 500 milliliter Disposable Filter Unit, pore size 0.2 micrometer (NALGENE, 450-0020). This is the 0.05 M $NaH_2PO_4$ stock solution. Weigh 3.55 grams sodium diphosphate ($Na_2HPO4$) (Sigma, cat#7907). Dilute in 400 milliliters of DEPC-treated water. Adjust volume to 500 milliliters. Filter through a 500 milliliter Disposable Filter Unit, pore size 0.2 micrometer (NALGENE, 450-0020). This is the 0.05 M $Na_2HPO_4$ stock solution. Mix 0.05 M $NaH_2PO_4$ and 0.05 M $NaH_2PO_4$ as described in Appendix C, Complex Buffers. Check pH and adjust it if necessary.

0.2 M Sodium Bicarbonate, pH 8.5 (Stock Solution for Elution Buffer)

Weigh 3.36 grams sodium bicarbonate (Fisher Scientific, cat# BP328-500). Dilute in 175 milliliters of DEPC-treated water. Adjust to pH 8.5 with hydrochloric acid. Add DEPC-treated water to 200 milliliters. Filter through a 250 milliliter Disposable Filter Unit, pore size 0.2 micrometer (NALGENE, 126-0020).

10 mM Sodium Bicarbonate, pH 8.5

Mix 1 milliliter of 0.2 M sodium bicarbonate, pH 8.5 and 19 milliliters of DEPC-treated water.

APPENDIX C

Preparation of Complex Buffers

TABLE 7

| Buffer | Chemical/Solvent | Amount | Final Concentration | Comments |
|---|---|---|---|---|
| Lysis Buffer:Binding Buffer | 6 M GuSCN | 72.3 ml | 4.34 M | Store at room temperature |
| | 0.35 M Tris-HCl, pH 6.4 | 13.2 ml | 46.2 mM | |
| | 0.5 M EDTA, pH 8.0 | 13.5 ml | 67.4 mM | |
| | Triton X-100, reduced | 1.1 g | 1.1% (w/v) | |
| 25 mM sodium phosphate Buffer, pH 7.0 | 0.05 M $NaH_2PO_4$ | 2.9 ml | 9.75 mM | pH should be 7.0 THIS IS IMPORTANT FOR LABELING |
| | 0.05 M $Na_2HPO_4$ | 4.6 ml | 15.25 mM | |
| | DEPC treated water | 7.5 ml | — | |
| Stop solution | 3 M NaAc pH 7.0 | 8.65 ml | 2.6 M | Store at room temperature |
| | 0.5 M EDTA, pH 8.0 | 1.35 ml | 67.4 mM | |

3. U-Protocol Testing Over S-Protocol

Five replicate preparations of *Bacillus thuringiensis* ssp. *subtoxicus* $H_6$ (subgroup *Cereus* B) vegetative cells were processed through S-Protocol; 3 replicate preparations of cells and 4 replicates of spores were processed through U-Protocol. Each sample contained $5.5\times10^8$ cells and $7.8\times10^9$ spores (6 mg of dry spores). 10-fold excess of spores relative to cells was used because vegetative cells contain ~10 times more rRNA than spores. Each aliquot of purified, fragmented and labeled nucleic acid was divided evenly (20 μl) between four replicate biochips for S-Protocol and three replicate biochips for U-Protocol, with each biochip containing two replicate probe sets. Therefore, each nucleic acid preparation was hybridized with eight and six sets of functional probes for S-Protocol and U-Protocol, respectively (n=3 or 4; psuedoreplicates=6 or 8). A total of 11 nucleic acid samples (samples VC-4, Table 8, was eliminated, see chapter 3.1) were hybridized with 84 biochips for 1 hour at room temperature. Hybridization patterns were recognized with latest version of customized *Bacillus cereus* subgroup recognition software "Microchip Reader" (Copyright: TXu 1-026-755). Equivalency between S-Protocol and U-Protocol was assessed by total nucleic acid yield, absolute and normalized hybridization signal intensity for all probes on the array, perfect to mismatch ratio (recognition value) and correct, automated biochip recognition.

3.1. Nucleic Acid Yield

Five replicate aliquots of vegetative cells were prepared according to S-Protocol, and the four samples with the highest nucleic acid yield (replicates VC-1, VC-2, VC-3 and VC-5) were carried forward for biochip hybridization. Replicate 2 showed a pronounced peak at 590 nm upon analysis, was obviously more colored than the other replicates, and generated the highest biochip background in empty gel elements. Therefore, it was conclude that Replicate 2 contained an excess of free dye after S-Protocol purification, fragmentation and labeling and was excluded from yield analysis (FIG. 7). Total nucleic acid yield and summary statistics for all other samples are shown in FIG. 7.

The vegetative cell data demonstrate that changes made during the development of the U-Protocol increased nucleic acid yield approximately 300% over S-Protocol, and decreased variability (standard deviation, SD) by 500% (SD ~50% for S-Protocol, ~10% for U-Protocol). The U-Protocol (but not S-Protocol) is also effective against spores. Because vegetative cells contain ~10 times more rRNA (hence, total nucleic acid) than spores, we took into the U-Protocol test experiment 14.2 fold more spores than vegetative cells. FIG. 7 shows that we isolated ~1.28 times more (total) nucleic acid from spores than from vegetative cells. Taking into account the difference in total nucleic acid content between spores and vegetative cells, this result demonstrates that the U-Protocol is equally efficient for spores and vegetative cells.

3.2. Biochip Signal Intensity

Samples described in FIG. 7 were carried forward for biochip hybridization. We used a standardized volume, 20 microliters, of purified, fragmented and labeled nucleic acid for each hybridization. As a result, U-protocol biochips received approximately 3 times more total nucleic acid than the corresponding S-Protocol biochips (FIG. 8). Biochips were hybridized for 1 hour at room temperature in guanidium buffer, as per S-Protocol hybridization standard operating procedures. All biochips were imaged on an 03-model custom-made portable imager (U.S. Pat. No. 6,620,623 B1) with an exposure time of 10 seconds. Hybridization signals were analyzed on a probe-by-probe basis, and also on an array-by-array basis. Each biochip data set contained 72 capture probes and 8 blank gel pads (background). Absolute, normalized hybridization signal for individual probes is shown in FIG. 1 and the average normalized hybridization signal over the entire biochip is shown in FIG. 2. Normalized data show equivalency in probe performance between S-Protocol (cells) and U-Protocol (cells). Also of note is the relative uniformity of signal intensity patterns for the U-Protocol, cells versus spores. These data support the conclusion that the U-Protocol was equally efficacious when challenged with spores or cells.

Figure 4:
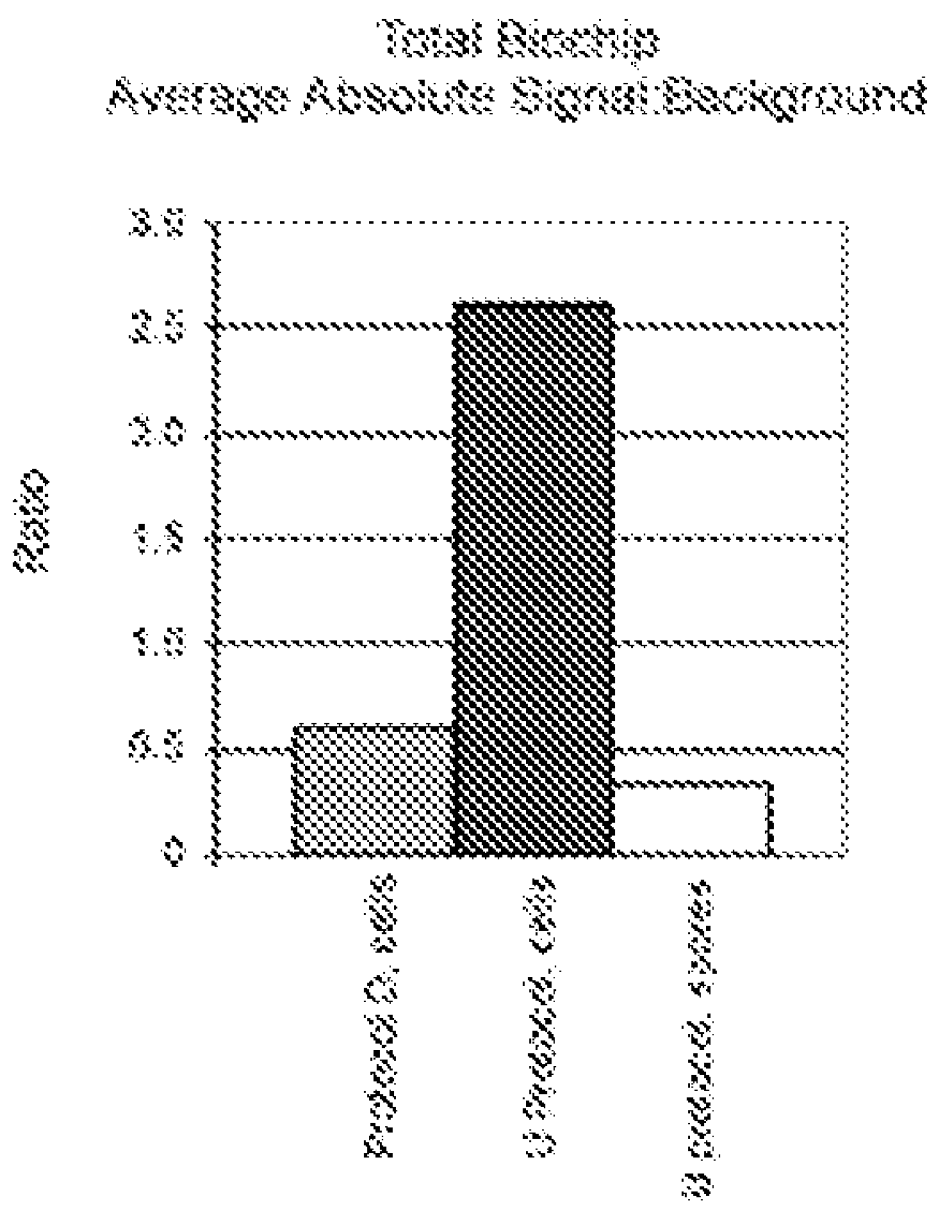

Probe-by-probe estimates of absolute signal to absolute background are illustrated in FIG. 3, and the average normalized signal over the entire biochip shown in FIG. 4. Plotted in this manner, the U-Protocol shows a 4-fold increase in signal-to-background relative to S-Protocol (FIG. 4). The increased signal-to-background of U-Protocol, vegetative cell results relative to the spore data are consistent with the proportional excess of target rRNA content in vegetative cells versus spores. The increase in absolute signal to absolute background for U-Protocol (cells) versus S-Protocol (cells) can be attributed mainly to the decreased quantity of free dye remaining in the extract (compare normalized signals in FIG. 2 to ratios in FIG. 4).

Hybridization signals and background can also be averaged across the entire biochip (rather than on a probe-by-probe basis). When analyzed in this manner, the average absolute signal and average background values provide information about the overall sensitivity of the method (from sample preparation through biochip readout). As shown in FIG. 8 and FIG. 4, a direct comparison of S-Protocol to the U-Protocol shows an average signal to background ratio of 0.6 (S-Protocol; SD ~60%) to 2.6 (U-Protocol; SD ~14%), which means that the U-Protocol is approximately 4.3-fold more sensitive than the original S-Protocol.

Figure 5:
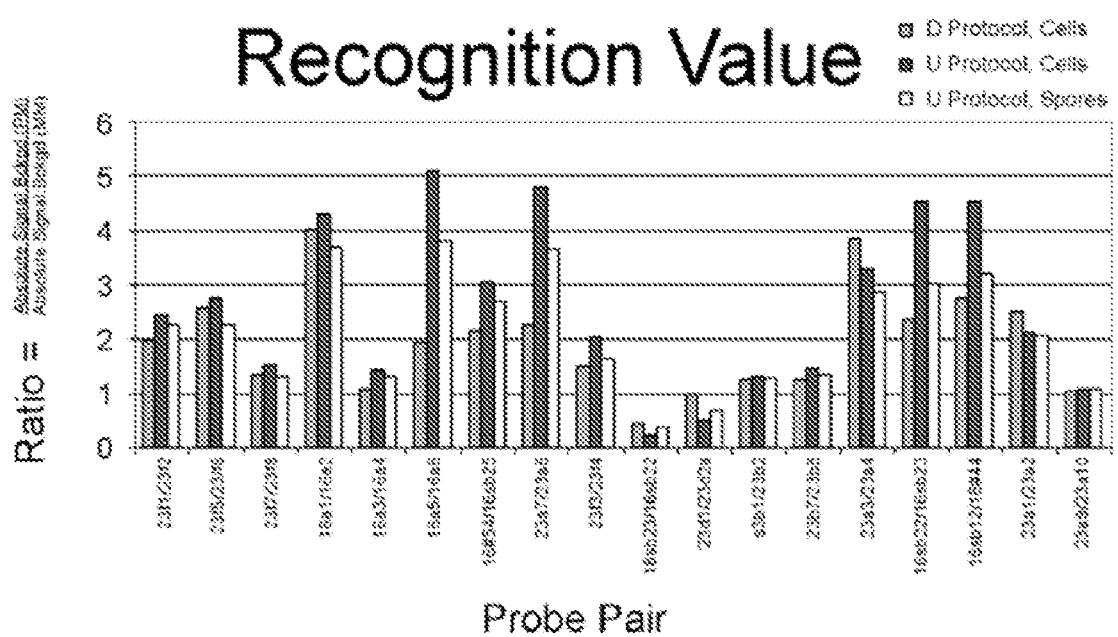

The decreased background realized in the U-Protocol demonstrably improves the recognition value (ratio of fluorescent signals from perfectly matched and mismatched probes) of specific probe pairs (Bavykin et al., 2008, Chem.-Biol. Interact., 172, 212-235) obtained with recognition software, as illustrated in FIG. 5.

Figure 6:
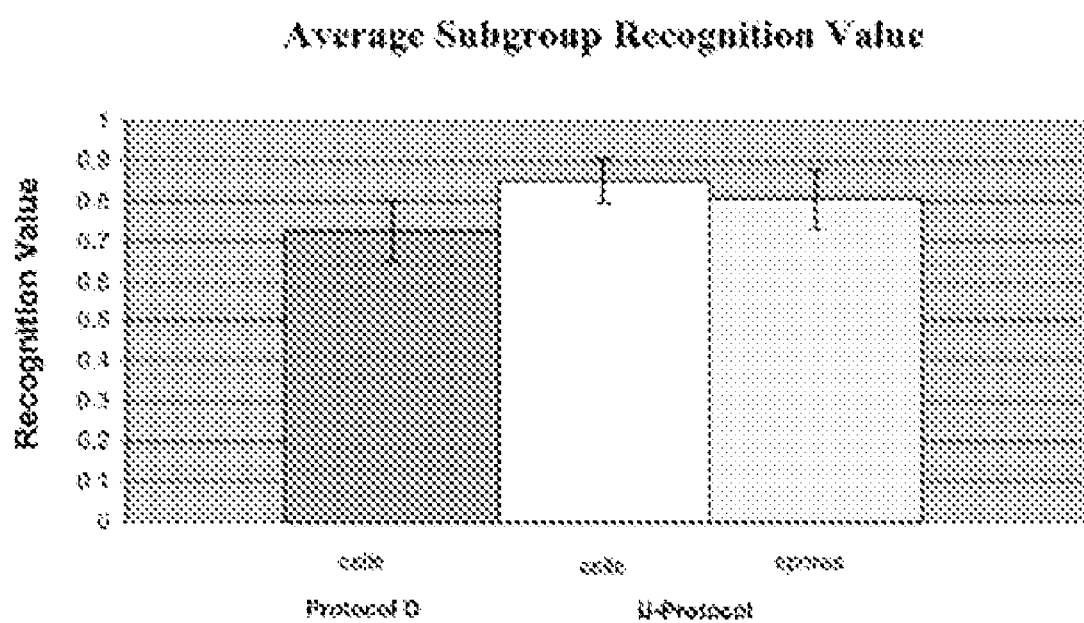

Equivalent performance was realized regardless of whether the protocols were challenged with cells or spores (FIG. 6 and Table 10). In practice, these data indicate that the U-Protocol should be able to detect and specifically recognize target organisms present at lower concentrations than currently required for successful recognition in S-Protocol. Stated another way, the U-Protocol requires fewer target cells than S-Protocol in order to achieve equivalent recognition performance. The absolute lower limit of detection sensitivity for the U-Protocol will need to be determined empirically.

Upon closer inspection of the U-Protocol data, we find that the average biochip background is 1.34 times higher for spores than for vegetative cells. This finding agrees with prior observations that the intensity of the biochip background increases proportionally with the amount of total labeled nucleic acid used for the hybridization. At the same time, the average absolute signal intensity for vegetative cells was 5.8 fold higher than the average absolute signal intensity for spores (FIG. 8). Given that we started with 1.44 times more total labeled nucleic acids from spores than from cells, the spore-normalized average absolute signal intensity for vegetative cells would be 8.35 (5.8×1.44=8.35). This finding also correlates with the expected (absolute) difference in rRNA content between spores and cells (i.e. ~10 times more rRNA in a vegetative cell than in a spore). Because spores and vegetative cells processed through the U-Protocol show background and absolute hybridization signals that are proportional to the expected rRNA content, these results indicate that rRNA isolated from spores and vegetative cells with U-Protocol were labeled and detected with the same efficiency.

3.3 Automated Recognition

The increased absolute signal and lower background associated with the U-Protocol relative to S-Protocol has a direct bearing on automated recognition performance. In particular, increasing the Average Signal/Average Background ratio becomes especially important for bacteria identification at low hybridization signals (e.g. absolute signals only 20% above background). As shown in FIG. 6 and FIG. 9, the recognition value for subgroup *Cereus* B in the U-Protocol (averaged over all extracts and all chips) was better than recognition values from S-Protocol, regardless of whether the U-Protocol was challenged with cells or spores.

CONCLUSIONS

From the foregoing validation study, we can conclude that 1) the U-Protocol is equally efficacious on cells and spores; 2) the U-protocol is more sensitive (higher signal, lower background) than S-Protocol; and 3) the U-protocol provides equivalent or better recognition values than S-Protocol. Equivalency of the two methods has therefore been demonstrated.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefor, is not intended to limit the claimed processes to any order except as may be specified in the claims. All ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as up to, at least, greater than, less than, and the like refer to ranges which can be subsequently broken down into sub-ranges as discussed above. Accordingly, the invention is limited only by the following claims and equivalents thereto.

All publications and patent documents cited in this application are incorporated by reference in their entirety for all purposes to the same extent as if each individual publication or patent document were so individually denoted.

What is claimed is:

1. A method for extracting nucleic acids from a biological sample comprising:
    providing a biological sample containing nucleic acids;
    applying the biological sample to a column;
    after applying the sample to the column, treating the column with a first protease containing mixture and allowing the first protease treated column to incubate;
    after treating the column with a first protease, centrifuging the column collecting the flow-through formed thereform and transferring the flow-through into an ethanol solution, forming a first collected flow-through;
    after collecting the first flow-through, washing the column with a first alcohol solution, centrifuging the column and discarding the flow-through formed therefrom;
    after washing the column with a first alcohol solution, treating the column with a lysozyme containing mixture and allowing the lysozyme treated column to incubate;
    after treating the column with a lysozyme containing mixture, centrifuging the column, collecting the flow-through formed therefrom and transferring the flow-through into an ethanol solution, forming a second collected flow-through;
    after collecting the second flow-through washing the column with a second alcohol solution, centrifuging the column and discarding the flow-through formed therefrom,
        after washing the column with a second alcohol solution treating the column with a second protease containing mixture and allowing the second protease treated column to incubate;
        after treating the column with a second protease containing mixture, centrifuging the column, collecting the flow-through formed therefrom and transferring the flow-through into an ethanol solution, forming a third collected flow-through;
        after collecting the third flow-through treating the column with a first magnesium free L:B buffer to release remaining nucleic acids;
    after the magnesium free L:B treatment, adding a $MgCl_2$ solution to the column and centrifuging the column;
    after adding the $MgCl_2$ solution to the column and centrifuging the column washing the column with the first, second, and third collected flow-throughs;
    after washing the column with the first, second, and third collected flow-throughs, adding an activated L:B buffer to the column to bind the released nucleic acids to the column, and then centrifuging the column; and
    eluting the nucleic acids to provide extracted nucleic acids.

2. The method of claim 1, wherein eluting the nucleic acids comprises: adding an elution buffer to the column, placing the column into a heat block and allowing the column to incubate, followed by centrifuging and retaining the flow-through therefrom containing the eluted nucleic acid, wherein the elution buffer comprises: 10 mM sodium carbonate.

3. The method of claim 1, wherein the protease containing mixture comprises: proteinase K, $H_2O$, and beta-mercaptoethanol.

4. The method of claim 1, wherein the lysozyme containing mixture comprises: lysozyme and $H_2O$.

5. The method of claim 1, wherein the column has an acidic pH, and wherein the sample is acidic upon application to the column.

6. The method of claim 1, wherein the biological sample is selected from the group consisting of: vegetative bacterial cells, spores and combinations thereof.

7. The method of claim 1, wherein the first, second, and third alcohol solutions comprise 75% ethanol.

8. The method of claim 1, wherein the method is completed in less than about 2 hours.

9. The method of claim 6, wherein the column has an acidic pH, the protease containing mixture comprises: proteinase K, $H_2O$, and beta-mercaptoethanol; the lysozyme containing mixture comprises: lysozyme and $H_2O$.

10. A method for extracting nucleic acids from a biological sample comprising:
    providing a biological sample containing nucleic acids;
    applying the biological sample to a column;
    after applying the sample to the column, treating the column with a first protease containing mixture and allowing the first protease treated column to incubate;
    after treating the column with a first protease, centrifuging the column collecting the flow-through formed thereform and transferring the flow-through into an ethanol solution, forming a first collected flow-through;
    after collecting the first flow-through, washing the column with a first alcohol solution, centrifuging the column and discarding the flow-through formed therefrom;
    after washing the column with a first alcohol solution, treating the column with a lysozyme containing mixture and allowing the lysozyme treated column to incubate;
    after treating the column with a lysozyme containing mixture, centrifuging the column, collecting the flow-through formed therefrom and transferring the flow-through into an ethanol solution, forming a second collected flow-through;
    after collecting the second flow-through washing the column with a second alcohol solution, centrifuging the column and discarding the flow-through formed therefrom,
    after washing the column with a second alcohol solution treating the column with a second protease containing mixture and allowing the second protease treated column to incubate;
    after treating the column with a second protease containing mixture, centrifuging the column, collecting the flow-through formed therefrom and transferring the flow-through into an ethanol solution, forming a third collected flow-through;
    after collecting the third flow-through treating the column with a first magnesium free L:B buffer to release remaining nucleic acids;

after the magnesium free L:B treatment, adding a $MgCl_2$ solution to the column and centrifuging the column;

after adding the $MgCl_2$ solution to the column and centrifuging the column washing the column with the first, second, and third collected flow-throughs;

after washing the column with the first, second, and third collected flow-throughs, adding an activated L:B buffer to the column to bind the released nucleic acids to the column, and then centrifuging the column;

labeling the nucleic acids within the column at the same time via a free radical-mediated process, resulting in labeled nucleic acids; and eluting the labeled nucleic acids from the column to produce extracted nucleic acids that are labeled.

11. A method for extracting nucleic acids from a biological sample comprising:

providing a biological sample containing nucleic acids;

applying the biological sample to an affinity matrix;

after applying the sample to the matrix, treating the affinity matrix with a first protease treatment, collecting the flow-through formed therefrom, and transferring the flow-through into an ethanol solution forming a first collected flow-through;

after the first protease treatment, treating the affinity matrix with a first alcohol treatment and discarding the flow-through formed therefrom;

after the first alcohol treatment, treating the affinity matrix with a lysozyme treatment containing mixture, collecting the flow-through formed therefrom and transferring the flow-through into an ethanol solution forming a second collected flow-through;

after the lysozyme treatment, treating the affinity matrix with a second alcohol treatment and discarding the flow-through formed therefrom, after the second alcohol treatment, treating the affinity matrix with a second protease treatment, collecting the flow-through formed therefrom and transferring the flow through into an ethanol solution forming a third collected flow-through;

after the second protease treatment, washing the affinity matrix with a first magnesium free L:B buffer to free any remaining nucleic acids;

after washing the matrix with a magnesium free L:B buffer, adding a $MgCl_2$ solution to the affinity matrix to bind the nucleic acids to the affinity matrix;

after washing the matrix with the $MgCl_2$ solution, washing the matrix with the first, second, and third collected flow-throughs;

after washing the matrix with the flow-throughs, washing the matrix with an activated L:B buffer to bind the released nucleic acids to the column, and then centrifuging the column; and eluting the nucleic acids to provide extracted nucleic acids.

12. The method of claim 11, wherein the affinity matrix is a nucleic acid affinity matrix selected from the group consisting of: affinity beads, affinity gels, affinity resins, affinity columns, affinity plates, and combinations thereof.

13. The method of claim 6, the protease containing mixture comprises: proteinase K, $H_2O$, and beta-mercaptoethanol; the lysozyme containing mixture comprises: lysozyme and $H_2O$.

14. The method of claim, 11, wherein eluting the nucleic acids comprises: adding an elution buffer to the affinity matrix, placing the matrix into a heat block and allowing the matrix to incubate, followed by centrifuging and retaining the flow-through therefrom containing the eluted nucleic acid, wherein the elution buffer comprises: 10 mM sodium carbonate.

15. The method of claim 11, further comprising labeling the nucleic acids within the affinity matrix prior to eluting the nucleic acids from the affinity matrix.

16. The method of claim 1, wherein the column is a silica column.

17. The method of claim 10, wherein the column is a silica column.

18. The method of claim 12, wherein the affinity matrix is a silica matrix.

* * * * *